United States Patent
Eusemann et al.

(10) Patent No.: US 10,165,995 B2
(45) Date of Patent: Jan. 1, 2019

(54) PHOTON COUNTING COMPUTED TOMOGRAPHY USING A COMBINATION OF CONTRAST AGENTS FOR SIMULTANEOUS VISUALIZATION OF ANATOMY AND A PLURALITY OF MATERIALS

(71) Applicant: Siemens Healthcare GmbH, Erlangen (DE)

(72) Inventors: Christian D. Eusemann, Malvern, PA (US); Matthew Kyle Fuld, Baltimore, MD (US)

(73) Assignee: Siemens Healthcare GmbH, Erlangen (DE)

( * ) Notice: Subject to any disclaimer, the term of this patent is extended or adjusted under 35 U.S.C. 154(b) by 224 days.

(21) Appl. No.: 15/301,074

(22) PCT Filed: Apr. 16, 2015

(86) PCT No.: PCT/US2015/026100
§ 371 (c)(1),
(2) Date: Sep. 30, 2016

(87) PCT Pub. No.: WO2015/161033
PCT Pub. Date: Oct. 22, 2015

(65) Prior Publication Data
US 2017/0020472 A1    Jan. 26, 2017

Related U.S. Application Data

(60) Provisional application No. 61/980,070, filed on Apr. 16, 2014.

(51) Int. Cl.
*A61B 6/00* (2006.01)
*A61B 6/03* (2006.01)
*A61B 6/06* (2006.01)

(52) U.S. Cl.
CPC .............. *A61B 6/481* (2013.01); *A61B 6/032* (2013.01); *A61B 6/06* (2013.01); *A61B 6/4241* (2013.01);
(Continued)

(58) Field of Classification Search
CPC ......... A61B 6/032; A61B 6/06; A61B 6/4241; A61B 6/4435; A61B 6/463; A61B 6/467; A61B 6/481; A61B 6/5211
See application file for complete search history.

(56) References Cited

U.S. PATENT DOCUMENTS

| | | | |
|---|---|---|---|
| 2004/0101088 A1 | 5/2004 | Sabol et al. | |
| 2004/0136491 A1* | 7/2004 | Iatrou | A61B 5/02007 378/4 |
| 2007/0189443 A1* | 8/2007 | Walter | A61B 6/032 378/4 |

FOREIGN PATENT DOCUMENTS

| | | |
|---|---|---|
| CN | 1517071 A | 8/2004 |
| CN | 101015461 A | 8/2007 |

(Continued)

OTHER PUBLICATIONS

Office action dated Nov. 2, 2018 in corresponding CN application No. 201580019884.8, 11 pages.

*Primary Examiner* — George Manuel

(57) ABSTRACT

A method for performing Photon Counting Computed Tomography (PCCT) using a combination of contrast agents includes configuring a PCCT device with a plurality of threshold values corresponding to a plurality of contrast agents. These contrast agents comprise a long-acting blood pool contrast agent and a nanoparticle contrast agent. The PCCT device is used to perform an imaging scan on an anatomical subject in the presence of the plurality of contrast agents to acquire image data. Next, the imaging data is processed into a plurality of datasets based on the plurality
(Continued)

of threshold values. The datasets comprise a first dataset corresponding to the long-acting blood pool contrast agent, and a second dataset corresponding to the nanoparticle contrast agent.

6 Claims, 3 Drawing Sheets

(52) U.S. Cl.
CPC ............ *A61B 6/4435* (2013.01); *A61B 6/463* (2013.01); *A61B 6/467* (2013.01); *A61B 6/5211* (2013.01)

(56) References Cited

FOREIGN PATENT DOCUMENTS

| WO | 2004008967 A1 | 1/2004 |
|---|---|---|
| WO | 2006084382 A1 | 8/2006 |

* cited by examiner

PHOTON COUNTING COMPUTED TOMOGRAPHY USING A COMBINATION OF CONTRAST AGENTS FOR SIMULTANEOUS VISUALIZATION OF ANATOMY AND A PLURALITY OF MATERIALS

CROSS-REFERENCE TO RELATED APPLICATIONS

This application claims priority to U.S. provisional application Ser. No. 61/980,070 filed Apr. 16, 2014, which is incorporated herein by reference in its entirety.

TECHNICAL FIELD

The present disclosure relates generally to methods, systems, and apparatuses for performing Photon Counting Computed Tomography using a combination of contrast agents for simultaneous visualization of anatomy and a plurality of materials. The disclosed technology may be applied, for example, to facilitate the simultaneous acquisition and visualization of anatomy including vasculature and macrophage-based hotspots.

BACKGROUND

Computed Tomography (CT) is an imaging technology that uses computer-processed X-ray beams to produce tomographic images of specific areas of a scanned object. Each x-ray beam comprises bundles of energy (or "photons") which, depending on the structure of the imaged material, may pass through, be absorbed by, or be redirected (i.e., scattered) by the structure. The degree to which an x-ray beam is reduced by an object during imaging is referred to as attenuation.

In order to differentiate two adjacent objects in a CT scan, there must be a density difference between the two objects. Where such a density difference does not naturally exist in the anatomy, a contrast enhancement material may be injected into the subject to create an artificial density difference in targeted areas to facilitate enhanced imaging. For example, a high density fluid may be used to fill the vasculature to differentiate it from the surrounding tissue.

There are many different types of contrast enhancement materials generally known in the art, each providing unique benefits. However, with conventional systems it is challenging to use multiple types of contrast enhancement materials simultaneously. For example, materials such as gadolinium and iodine have traditionally been used for vascular visualization. For tissue enhancement, materials such as nanoparticles may be used to bind to an area of interest (e.g., macrophages to target anatomical "hot spots" of chronic inflammation). Unfortunately, these nanoparticle contrast agents require some time before binding at the site of interest, during which time the vascular contrast agents are washed out and are no longer useful for imaging. This leads to a very low contrast-to-noise ratio (CNR) for tissue and vasculature.

Accordingly, it is desired to produce a technique for simultaneously acquiring image data corresponding to multiple contrast agents using a single scan.

SUMMARY

Embodiments of the present invention address and overcome one or more of the above shortcomings and drawbacks, by providing methods, systems, and apparatuses related to the use of Photon Counting CT (PCCT) with a combination of contrast agents for simultaneous visualization of anatomy and other materials. Briefly, a PCCT device is configured with a plurality of threshold values corresponding to the different contrast agents. In some embodiments, these contrast agents include long-acting blood pool agents and nanoparticles. Data acquired by the PCCT is separated into windows (or "bins") based on the threshold values, allowing for the independent processing and reconstruction of datasets corresponding to the different contrast agents. The techniques described herein may be applied, for example, to facilitate the simultaneous acquisition and visualization of anatomy including vasculature and macrophage-based hot spots.

According to some embodiments, a method for performing PCCT using a combination of contrast agents includes configuring a PCCT device with a plurality of threshold values corresponding to a plurality of contrast agents. These contrast agents comprise a long-acting blood pool contrast agent and a nanoparticle contrast agent. The PCCT device is used to perform an imaging scan on an anatomical subject in the presence of the plurality of contrast agents to acquire image data. Next, the imaging data is processed into a plurality of datasets based on the plurality of threshold values. The datasets comprise a first dataset corresponding to the long-acting blood pool contrast agent, and a second dataset corresponding to the nanoparticle contrast agent. In some embodiments, the contrast agents include at least one short-lived contrast agent (e.g., gadolinium or iodine) that is designed to washout of the anatomical subject within 10 minutes following injection. The plurality of datasets may then include datasets corresponding to this short-lived contrast agent.

Images may be reconstructed based on the datasets described in the aforementioned method. For example, in some embodiments, a plurality of images is reconstructed based on the datasets. These images include a first set of images corresponding to the long-acting blood pool contrast agent and a second set of images corresponding to the nanoparticle contrast agent. Then, one image from the first set of images and one image from the second set of images may be simultaneously presented on a display.

In some embodiments the PCCT device in the aforementioned method processes the imaging data into the datasets based on the threshold values by first identifying a plurality of electrical pulses in the imaging data. These pulses are then converted into measurement voltages. An energy level is assigned to each of the plurality of electrical pulses based on a comparison of the measurement voltages with threshold voltages corresponding to the threshold values. Then, the datasets are created based on the energy level assigned to each of the electrical pulses. In one embodiment, each respective dataset includes a photon count value corresponding to a distinct one of the threshold values.

According to other embodiments for performing PCCT using a combination of contrast agents includes configuring a PCCT device with a plurality of threshold values corresponding to a plurality of contrast agents. These contrast agents may include, for example, at least two long-lived contrast agents designed to remain in an anatomical subject for at least 12 hours following injection into the anatomical subject, and one or more short-lived contrast agents designed to washout of the anatomical subject within 10 minutes following injection into the anatomical subject. For example, the long-lived contrast agents may comprise a long-acting blood pool contrast agent and a nanoparticle contrast agent (e.g., gold-based), while the short-lived contrast agents may be an iodine-based contrast agent or a gadolinium-based contrast agent. Once configured, the PCCT device may be used to perform an imaging scan on the anatomical subject in the presence of the contrast agents to acquire image data. This imaging data may then be processed into datasets based on the threshold values, with the datasets comprising at least one dataset for each of the contrast agents. Once the datasets have been acquired, they may be used to reconstruct a set of images for each of the contrast agents. Then, the images from each set may be simultaneously presented on a display.

According to other embodiments, an imaging system includes a gantry, an x-ray source, a detector, and an evaluation unit. The x-ray source is configured to rotate with the gantry around a subject. The detector comprises sensors which are configured to convert radiation quanta into a plurality of electrical pulses. The evaluation unit is configured to process electrical pulses into datasets according to one or more adjustable energy thresholds. These adjustable energy thresholds comprise a first threshold which is optimized for energy levels corresponding to a long-acting blood pool contrast agent, and a second threshold which is optimized for energy levels corresponding to long-acting a nanoparticle contrast agent. In some embodiments, the evaluation unit comprises a plurality of pulse-height comparator circuits configured to compare height information corresponding to each of the electrical pulses to the adjustable energy thresholds to separate the electrical pulses into datasets.

In some embodiments, the aforementioned imaging system includes additional components. For example, in one embodiment, the imaging system includes an imaging computer which is configured to reconstruct images based on the datasets. These images may include, for example, a first set of images corresponding to the long-acting blood pool contrast agent, and a second set of images corresponding to the nanoparticle contrast agent. In one embodiment, the imaging system includes a display which is configured to simultaneously present an image from the first set of images and an image from the second set of images. In one embodiment, the display is further configured to present a graphical user interface allowing display characteristics associated with each image to be modified without changing display characteristics associated with other displayed images.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses for performing Photon Counting CT (PCCT) using a contrast combination of long-acting blood pool agents and nanoparticles for simultaneous visualization of anatomy and other materials. Briefly, a PCCT device allows the compartmentalization of detected X-ray photons into energy bins. Using the techniques described herein, this compartmentalization is used for selective contrast material detection by recognizing material-specific energy distributions. Thus, the spatial distribution of contrast agents may be quantified on a pixel basis within a single scan.

Figure 1:
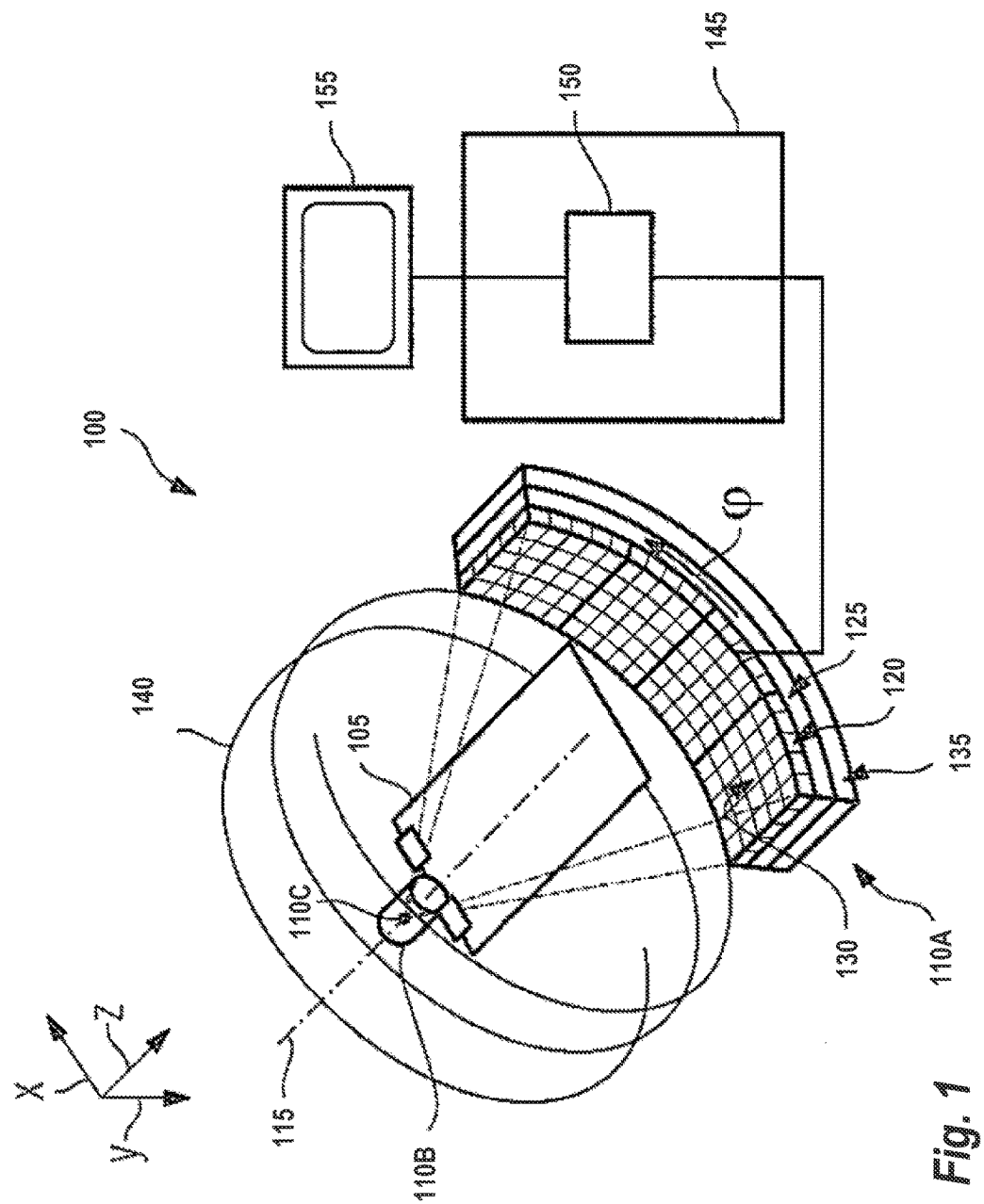
FIG. 1 provides an illustration of a Photon Counting CT (PCCT) imaging system, as may be used in some embodiments of the present invention.

FIG. 1 provides illustrates a PCCT imaging system 100, as may be used in some embodiments of the present invention. Briefly, an array of multiple detector elements (pixels) is used for directly converting semiconductor material. A detected radiation quantum generates a charge pulse, which is converted by the detector electronics into a measurement voltage which is compared in one or more comparators with different energy levels representing threshold voltages in the respective detector element. In this way, a detected photon can be assigned a certain energy and the photon is counted accordingly.

The imaging system 100 comprises a subject support table 105 for supporting a subject to be examined. Additionally, the system 100 includes a gantry (not illustrated in FIG. 1) with a recording system comprising an X-ray source 110B and a counting detector 110A. The recording system is mounted within the gantry such that it can rotate about a system axis 115. The X-ray source 110B and counting detector 110A are aligned opposite one another such that X-ray radiation emitted by the focus 110C of the X-ray source 110B during operation impinges on the detector 110A. A collimator 120 is placed in front of the detector to suppress the scattered radiation created in the subject. This collimator may be configured to only pass to the detector 110A the primary radiation that was emitted by the focus 110C and attenuated as a function of the subject penetration.

In principle, both an indirect-conversion, i.e. optically counting, detector and a direct-conversion detector can be used as a counting detector 110A. In the example of FIG. 1, the counting detector 110A is a direct-conversion detector integrated with a semiconductor layer 125. The semiconductor layer 125 may comprise any material generally known in the art which is suitable for direct-conversion applications. Semiconductor materials having such properties include, without limitation, CdTe, CdZnTe, CdZnTeSe, and CdZnTeSe compounds. In the semiconductor layer 125, the incident X-ray quanta are converted into free charge carriers, registered as electrical signals by way of downstream readout electronics as a result of a forced charge carrier transport in an electrical field, and converted into an electrical pulse, which is evaluated by way of an evaluation unit 135.

The detector 110A is subdivided into individual sensors 130 or pixels for spatially-resolved acquisition of the absorption events. The sensors 130 are configured to convert radiation quanta into electrical pulses. The evaluation unit 135 is configured to count these pulses using one or more adjustable energy thresholds. Physically, these thresholds may be implemented by voltages that are fed into pulse-height comparator circuits (not shown in FIG. 1). The height of each pulse is compared with a given threshold value and a count is registered by the comparator if the pulse height exceeds the threshold value. The counts in the energy window defined by two adjacent threshold values (as referred to as a "bin") may be determined by subtracting counts in counters from the two threshold values.

In order to record an image of an examination region, projections are registered from a plurality of different projection directions when the recording system 110A, 110B rotates about the system axis 115, wherein the detector 110A registers count values Z1, Zk, Z2 for each projection and for each sensor 130. In the case of a helical scan, there is, for example simultaneously, a continuous adjustment of the subject support table 105 in the direction of the system axis 115 during a rotation of the recording system 110A, 110B. In this type of scan, the X-ray source 110B and the detector 110A therefore move along a helical path 140 around the subject. A correction unit included in the evaluation unit 135 establishes at least one corrected count value Zkorr from the count values Z1, Zk, Z2. The count values Z1, Zk, Z2, and Zkorr are subsequently serialized in a sequencer and transmitted to an imaging computer 145. The imaging computer 145 contains a reconstruction unit 150 with one or more processors configured to reconstruct an image, e.g. in the form of a slice image of the subject, from the count values Z1, Zk, Z2, Zkorr. The resultant image can then be displayed on a display unit 155 (e.g. a video monitor) operably coupled to the imaging computer 145. In some embodiments, the display unit 155 provides a Graphical User Interface (GUI) which allows the user to interact and change various characteristics of the display of the image.

The system illustrated in FIG. 1 distinguishes between different materials based on x-ray attenuation, according to the following equation:

$$I = I_0 e^{-\mu x}$$

In this equation, I and $I_0$ represents the transmitted and incident intensity of the x-ray, respectively. In the exponent, x represents the thickness of the absorbing material and $\mu$ is a mass attenuation coefficient. The mass attenuation coefficient is proportional to the atomic number of the material (K). This relationship can be used to select optimal contrast materials for imaging by selecting materials corresponding to high atomic numbers. Each contrast material has a known relationship between its mass attenuation coefficient and its relationship to photon energy.

Typically, with contrast agents, photoelectric absorption results in a sudden increase in the attenuation coefficient of photons occurring at a photon energy just above the binding energy of the K shell electron of the atoms interacting with the photons. The area at which this sudden increase occurs is referred to as the k-shell binding energy or "k-edge." This k-edge of the contrast material may be used to determine the threshold values to be applied by the PCCT to distinguish the material during the scan. For example, gadolinium is known to have an atomic number of 64 and a k-edge of 50.2 kiloelectron-volts (keV). Based on this knowledge, one or more thresholds can be adjusted in the scanner to specifically distinguish the gadolinium from the surrounding tissue.

Figure 2:
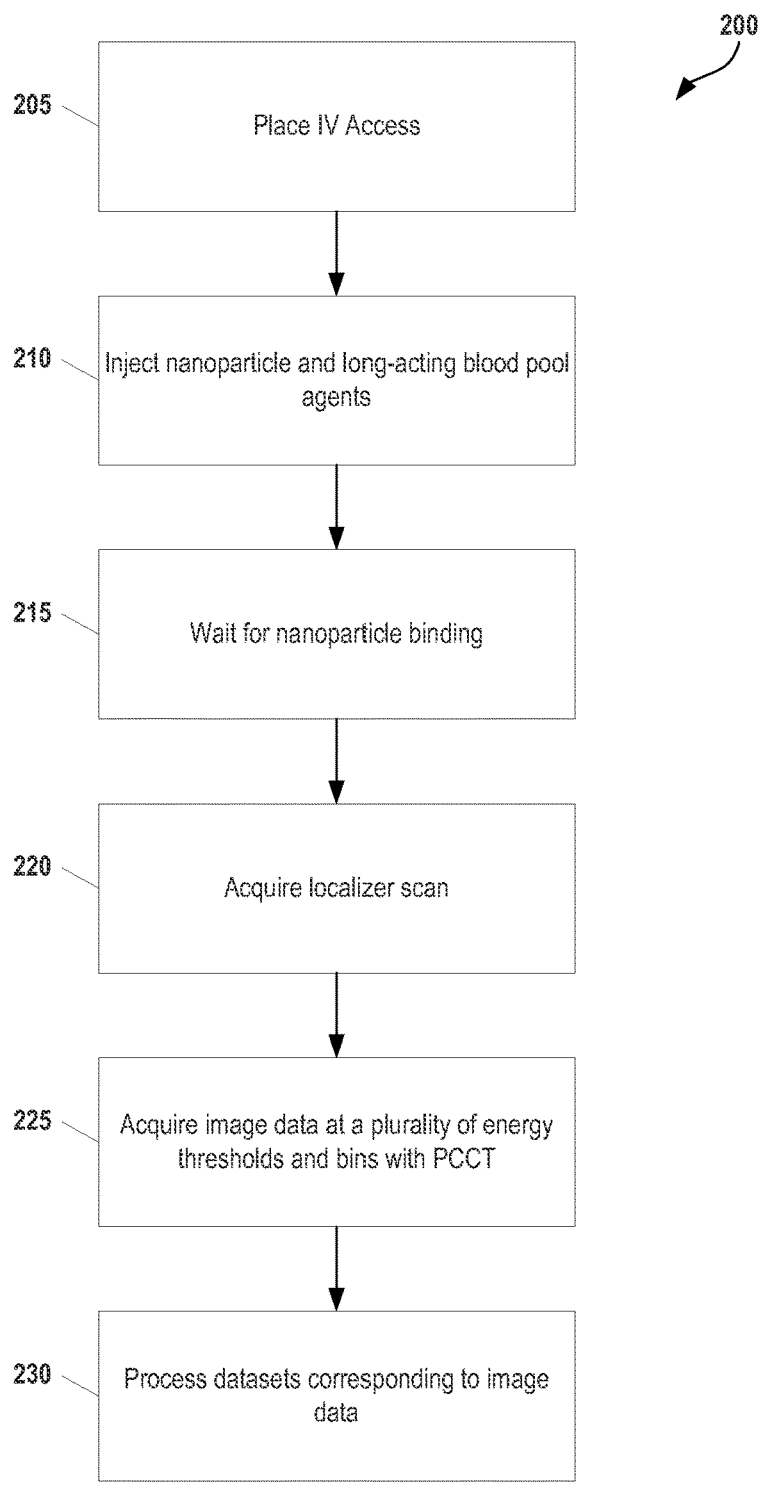
FIG. 2 provides an illustration of a process for performing PCCT imaging with long-acting blood pool agents and nanoparticles, according to some embodiments.

FIG. 2 provides an illustration of a process 200 for performing PCCT imaging with long-acting blood pool agents and nanoparticles, according to some embodiments. At step 205, an intravenous (IV) access device is implanted under the subject's skin. As is understood in the art, such devices allow medications, fluids, and other substances to be directly delivered into larger veins and can be left in for long periods of time. The device is typically a small-flexible tube placed in a location in the subject that is easily accessible to medical staff. In the context of the process 300 illustrated in FIG. 3, this IV access device will facilitate the administering of various contrast agents.

Next, at step 210, nanoparticles and long-acting blood pool agents are injected using the IV access device. As is understood in the art, nanoparticles and long-acting blood pool agents are both examples of contrast agents. Various types of nanoparticles generally known in the art may be injected at step 210 including, without limitation, gold nanoparticles and particles tagged with materials such as bismuth. Similarly, the long-acting blood pool agents may be iodinated lipids or any other substance providing contrast enhancement over a long period of time (typically 12-24 hours). Nanoparticle surfaces have a strong binding affinity towards thiol, disulfide and/or amine groups, which allow surface conjugation with various biomolecules. In turn, this allows for particular portions of anatomy to be targeted during imaging. Long-lasting agents have a molecule that can be scanned and will highlight the distribution of the entire blood pool, providing an indication of the distribution of blood throughout the body. Thus, used in combination, nanoparticles and long-lasting blood pool agents provide the ability to enhance various aspects of the subject's anatomy simultaneously during imaging.

As noted above, nanoparticles bind to targeted anatomical areas in the subject. This process is not immediate, thus, at step 215, the process 200 is temporarily suspended to allow for the binding process to be completed. However, it should be noted that, once binding is completed, the nanoparticles will remain bound for a long-time in the subject. Thus, steps 205-215 may be completed several hours in advance of PCCT imaging.

Continuing with reference to FIG. 2, at step 220, the PCCT is used to acquire a localizer scan. As understood in the art, a localizer scan is a digital image acquisition created while the x-ray source is stationary and the table moves through the scan field of the gantry. A localizer scan results in the acquisition of one or more localizer images which are similar to images acquired with conventional radiograph devices. Thus, in contrast to images acquired with PCCT, the localizer images are not cross-sectional in nature. Following acquisition, the technologist administering the scan may use the localizer images to perform tasks such as prescribing the location of the cross-sectional slices, ensuring proper placement of the subject on the scanner table, selecting the optimal display field of view for the PCCT scan, and correcting for image center.

Following the localizer scan, at step 225, the PCCT device is used to acquire image data at a plurality of energy thresholds and bins configured according to the selected contrast materials. As described above with reference to FIG. 1, an X-ray detector operated in photon counting mode applies energy discrimination by threshold values for each individual pixel. In order to distinguish the nanoparticles and blood pool agents applied at step 210, threshold values are pre-set for these two types of contrast agents. These threshold values may be based on, for example, the k-edge values associated with the nanoparticle and blood pool agent substances. For example, for gold nanoparticles, appropriate threshold values may be selected within the range of 70-80 keV. For iodine-based blood pool agents, the threshold values may be selected within the range of 30-40 keV.

Once the data has been acquired, at step 230, it is processed into at least three datasets: a dataset containing anatomy bound to the nanoparticles, a dataset representative of blood flow as indicated by the blood pool agents, and a dataset of anatomy not otherwise affected by the contrast agents. Each dataset can then be used to reconstruct images using any CT reconstruction generally known in the art. In some embodiments, the same reconstruction technique is used for all the datasets. In other embodiments, different reconstruction techniques may be used based on the contents of the dataset. Thus, for example, reconstruction routines optimized for nanoparticle-based imaging may be used for dataset containing anatomy bound to the nanoparticles, while other reconstruction techniques are applied to the remaining datasets.

Following reconstruction, the resulting images may be displayed (as described in FIG. 1) or stored for later processing. It should be noted that, because the datasets are independent, their corresponding images are also independent. This allows a user to selectively view images corresponding to one of the datasets in isolation. Alternatively, images from the different datasets may be overlaid and different image display features (e.g., brightness, contrast, etc.) may be applied to the different types of images independently to enhance particular portions of the subject's anatomy.

Figure 3:
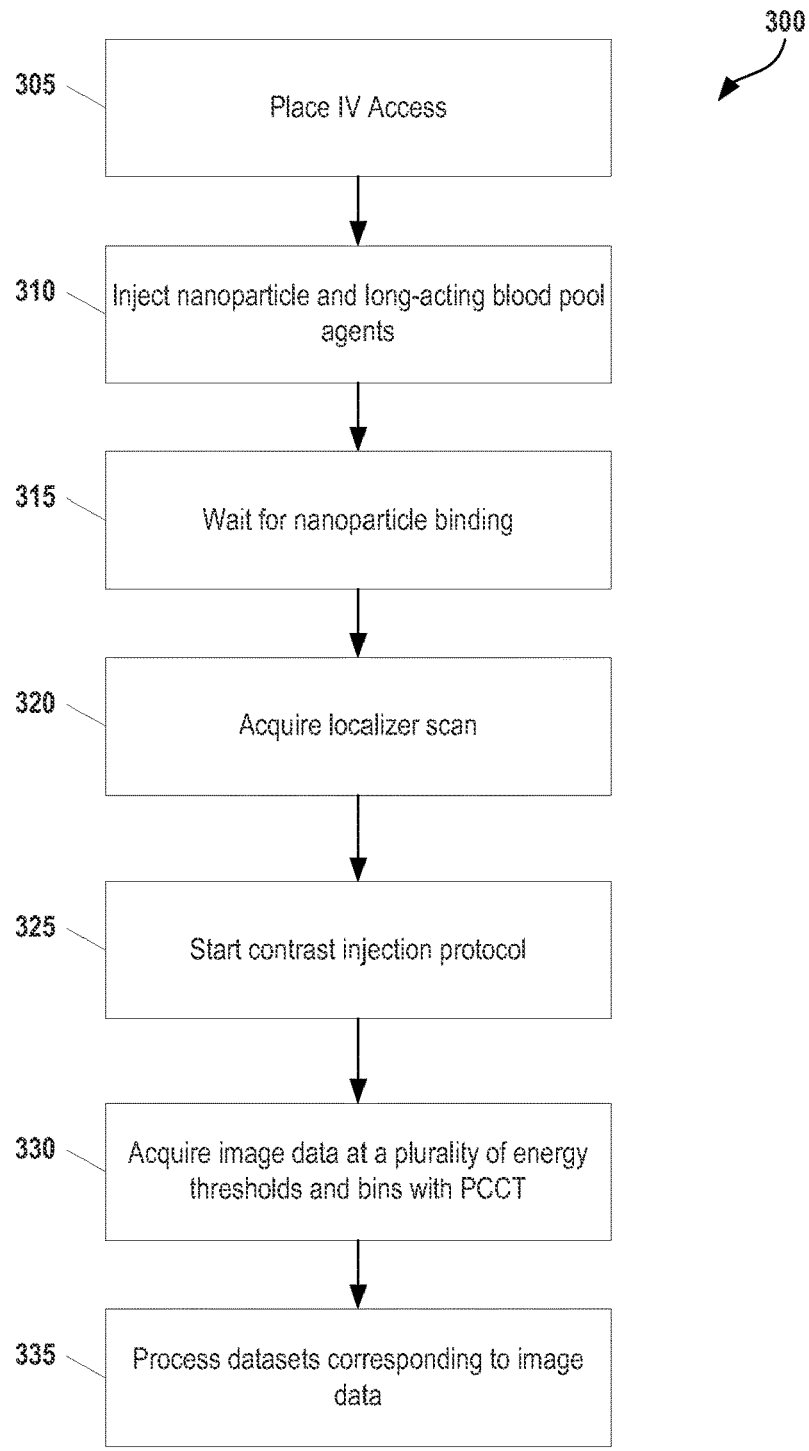
FIG. 3 provides an illustration of a process for performing PCCT imaging with long-acting blood pool agents, nanoparticles and conventional IV contrast agents, according to some embodiments.

The general process of distinguishing various contrast agents illustrated in FIG. 2 can scale with the number of thresholds available at the scanner. FIG. 3 provides an illustration of a process 300 for performing PCCT imaging with long-acting blood pool agents, nanoparticles and conventional IV contrast agents, according to some embodiments. As with FIG. 2, the initial step 305 of FIG. 3 is to implant an IV access device under the subject's skin to use in the administering of various contrast agents. At step 310, nanoparticles and long-acting blood pool agents are injected into the subject using the IV access device. Then, at step 315 the nanoparticles proceed to bind with the targeted portion of the subject's anatomy.

Continuing with reference to FIG. 3, at step 320, a localizer scan is performed to acquire one or more localizer images. At step 325, a short-lived contrast agent is applied. This short-lived contrast agent may be, for example, an iodine-based substance such as, without limitation, Diatrizoate, Metrizoate, Ioxaglate, and Iodixanol. Unlike the nanoparticles and long-acting blood pool agents injected at 310, the short-lived contrast agent will be filtered out of the subject's systems by his or her liver and kidneys within a few minutes. Thus, this injection should take place immediately preceding imaging. At step 330, this imaging is performed in a manner similar to the imaging performed at step 225 of FIG. 2 to yield a plurality of datasets. However, for the example of FIG. 3, threshold values are set for the three different types of contrast agents. Once the data has been acquired, at step 335, it is processed into at least four datasets: a dataset containing anatomy bound to the nanoparticles, a dataset representative of blood flow as indicated by the blood pool agents, a dataset representative of the presence of the short-lived contrast agents, and a dataset of anatomy not otherwise affected by the contrast agents. Each dataset may then be reconstructed into images for display or storage for later viewing. It should be noted that the only limitation on expanding the process illustrated in FIG. 3 is the number of thresholds supported by the scanner. Thus, as the number of thresholds increases, the number of different contrast agents that may be simultaneously imaged likewise increases.

It is also important to note that Photon Counting CT is only one of the potential modalities that might benefit from a mixture of nanoparticles and long lasting contrast, as described in FIGS. 2 and 3. This mixture might also be used with other imaging modalities such as, without limitation, magnetic resonance (MR), ultrasound, positron emission tomography (PET), single-photon emission computed tomography (SPECT).

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing systems, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity. Also, while some method steps are described as separate steps for ease of understanding, any such steps should not be construed as necessarily distinct nor order dependent in their performance.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for performing Photon Counting Computed Tomography (PCCT) using a combination of contrast agents, the method comprising:
    configuring a PCCT device with a plurality of threshold values corresponding to a plurality of contrast agents, the plurality of contrast agents comprising:
        at least two long-lived contrast agents designed to remain in an anatomical subject for at least 12 hours following injection into the anatomical subject, and
        one or more short-lived contrast agents designed to washout of the anatomical subject within 10 minutes following injection into the anatomical subject;
    using the PCCT device to perform an imaging scan on the anatomical subject in the presence of the plurality of contrast agents to acquire image data;
    processing the imaging data into a plurality of datasets based on the plurality of threshold values, the plurality of datasets comprising at least one dataset for each of the plurality of contrast agents.

2. The method of claim 1, wherein the at least two long-lived contrast agents comprise a long-acting blood pool contrast agent and a nanoparticle contrast agent.

3. The method of claim 2, wherein the nanoparticle contrast agent comprises a gold-based material.

4. The method of claim 3, wherein the one or more short-lived contrast agents is an iodine-based contrast agent or a gadolinium-based contrast agent.

5. The method of claim 2, further comprising:
    reconstructing a plurality of images based on the plurality of datasets, the plurality of images comprising:
        a first set of images corresponding to the long-acting blood pool contrast agent,
        a second set of images corresponding to the corresponding to the nanoparticle contrast agent, and
        a third set of images corresponding to the one or more short-lived contrast agents.

6. The method of claim 5, further comprising:
    simultaneously presenting a first image from the first set of images, a second image from the second set of images, and a third image from the third set of images.

* * * * *